United States Patent
Wang et al.

(10) Patent No.: US 7,531,658 B2
(45) Date of Patent: May 12, 2009

(54) PROCESS FOR THE PREPARATION OF 17-N-SUBSTITUTED-CARBAMOYL-4-AZA-ANDROST-1-EN-3-ONES

(75) Inventors: Zhi-Xian Wang, Brantford (CA); Alfredo Paul Ceccarelli, Brantford (CA); Mohammed Abdul Raheem, Brantford (CA); Bhaskar Reddy Guntoori, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 174 days.

(21) Appl. No.: 11/335,782

(22) Filed: Jan. 20, 2006

(65) Prior Publication Data

US 2007/0173523 A1     Jul. 26, 2007

(51) Int. Cl.
*C07D 221/18*    (2006.01)

(52) U.S. Cl. ............................................... 546/77

(58) Field of Classification Search ................ 560/27; 562/466; 564/139; 546/77
See application file for complete search history.

(56) References Cited

U.S. PATENT DOCUMENTS

| | | |
|---|---|---|
| 4,760,071 A | 7/1988 | Rasmusson et al. |
| 5,021,575 A | 6/1991 | King et al. |
| 5,116,983 A | 5/1992 | Bhattacharya et al. |
| 5,468,860 A | 11/1995 | Dolling et al. |
| 5,652,365 A | 7/1997 | McCauley et al. |
| 5,670,643 A | 9/1997 | Davis et al. |
| 2005/0059692 A1 | 3/2005 | Reddy et al. |

FOREIGN PATENT DOCUMENTS

| | | |
|---|---|---|
| EP | 0 271 220 B1 | 1/1992 |
| EP | 0 599 376 B1 | 4/1998 |
| WO | WO 2005/066195 A1 | 7/2005 |

*Primary Examiner*—Taofiq A Solola

(57) ABSTRACT

The present invention relates to a process for producing 17-N-substituted-carbamoyl-4-aza-androst-1-en-3-ones of formula 1, including Finasteride and Dutasteride.

39 Claims, No Drawings

PROCESS FOR THE PREPARATION OF 17-N-SUBSTITUTED-CARBAMOYL-4-AZA-ANDROST-1-EN-3-ONES

FIELD OF THE INVENTION

The present invention relates to a process for producing 17-N-substituted-carbamoyl-4-aza-androst-1-en-3-ones of formula 1, including Finasteride and Dutasteride.

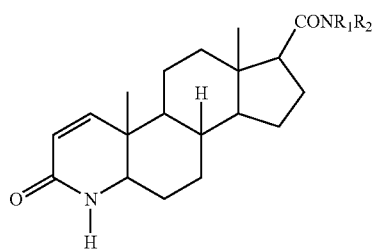

1

Finasteride: $R_1$=H, $R_2$=t-Butyl
Dutasteride: $R_1$=H, $R_2$=2,5-bis(trifluoromethyl)phenyl

BACKGROUND OF THE INVENTION

The enzyme testosterone 5-α-reductase is known to convert testosterone to dihydrotestosterone, DHT in the human body. DHT has been implicated in causing enlargement of the prostate and benign prostatic hyperplasia (BPH), which leads to malignant conditions such as prostate cancer. Accordingly, it is desirable to inhibit the action of testosterone 5-α-reductase, and a number of 4-aza-steroids have been reported to be active in this respect. In particular, two 4-aza-steroids 5-α-reductase inhibitors, namely Finasteride (Proscar™) and Dutasteride (Avodart™) have reached the market for the treatment of BPH. A major advantage of these compounds is that they do not bind with androgen receptor sites. Specifically for Finasteride, it doesn't possess androgenic, anti-androgenic, or other steroid hormone-related properties. Therefore, Finasteride can lower the DHT level in humans without interfering with the testosterone levels. Finasteride has also been studied on hair growth, hair cycle stage, and serum testosterone and dihydrotestosterone, and it was found that Finasteride increased hair weight. Finasteride, marketed with the trade name Propecia™, is the first and only drug to date to be approved by the FDA for the treatment of male pattern hair loss on the vertes (top of head) and anterior mid-scalp area (middle front of head).

Finasteride and Dutasteride may be prepared by various known methods that involve the steps of converting the 17β-carboxyl group into t-butylcarbamoyl and 2,5-bis(trifluoromethyl)phenylcarbamoyl groups respectively and introducing the 1,2-double bond by dehydrogenation.

Numerous methods have been disclosed for converting the 17β-carboxyl group to an amide. For instance, U.S. Pat. No. 4,760,071 discloses a method of preparing a 17β-t-butylcarbamoyl derivative by converting the 17β-carboxyl group into a pyridylthio ester which is subsequently reacted with the amine. However, this method requires the use of expensive 2,2'-dithiopyridine.

US Patent Application 2005/0059692 A1 discloses a process for synthesizing Dutasteride by reacting the 17β-carboximide group with 2-iodo-1,4-bis(trifluoromethyl)benzene. However, this method uses insoluble copper halide that requires repeated washing and filtering to remove.

U.S. Pat. No. 5,670,643 offers a method to convert the 17β-carboxyl group into an acid chloride and reacting the acid chloride with t-butylamine. However, this method uses toxic thionyl chloride, which is difficult to handle, and the product is difficult to purify.

U.S. Pat. Nos. 5,468,860 and 5,652,365 and EP patent 599,376 disclose a method of reacting an organomagnesium halide with t-butylamine to obtain a t-butylaminomagnesium halide, and then reacting the t-butylaminomagnesium halide with a 17β-carboalkoxy compound. However, this method suffers from the disadvantage that the organomagnesium halide is expensive and moisture-sensitive.

EP patent 271,200 describes a method to convert the 17β-carboxyl group into a hydroxybenzothiazolyl ester or imidazolide which is subsequently reacted with t-butylamine. However, this method has the deficiency that the reaction yields a product of low purity.

There are also several synthetic methods reported in the prior art for introducing a 1,2-double bond into 4-azasteroids. For example, U.S. Pat. No. 4,760,071 discloses that dehydrogenation is carred out using benzeneseleninic anhydride in refluxing chlorobenzene. However, benzeneseleninic acid anhydride is a highly toxic material and is unsuitable for industrial production.

U.S. Pat. No. 5,116,983 teaches a method whereby the 1,2-double bond was introduced by refluxing with 2,3-dichloro-5,6-dicyano-4-benzoquinone (DDQ) and bis(trimethsilyl)-trifluoroacetamide (BSTFA) in dioxane. The disadvantages of these procedures include the facts that BSTFA is very expensive and DDQ is highly toxic. The latter deficiency complicates the purification to obtain a pharmaceutically acceptable product.

U.S. Pat. No. 5,021,575 discloses a four step process comprising:

a) reacting a 17β-substituted-3-oxo-4-azasteroid with oxalyl chloride;

b) monobrominating the oxalylated intermediate at the 2-position;

c) reacting the brominated product with ethylenediamine or 2-(N-methylamino)ethanol to produce α- and β-2-monobrominated isomers; followed by d) dehydrobromination of the product of (c) which results in the introduction of a double bond at the 1,2-position.

However, this process suffers from various disadvantages including the fact that the monobromination reaction (b) must be performed at a very low temperature (−70° C. in example 1) and with very gradual addition of a stoichiometrically precise quantity of bromine to prevent contamination of the product due to undesired reaction by-products. The very low temperatures and slow addition of bromine required in this step reduce the utility of the process for large scale production.

WO 2005/066195 discloses a process comprising sulfenylation, oxidation and elimination to introduce the 1,2-double bond. However, the sulfenylation step requires a strong base and harsh reaction conditions (refluxing with a strong base in tetrahydrofuran for more than 16 hours), which may cause decomposition and epimerization.

Accordingly, there is a need to develop improved methods for preparing the amide group from 17β-carboxyl group and introducing a 1,2-double bond into a 3-oxo-4-aza-steroid.

SUMMARY AND DETAILED DESCRIPTION OF THE INVENTION

According to one aspect of the invention, a process is provided for the preparation of a 17-amido-3-oxo-4-azasteroid of formula 2,

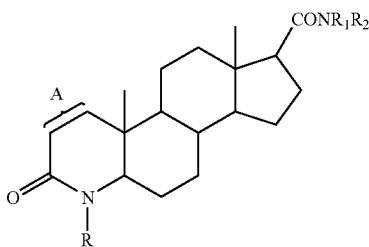

wherein R is selected from hydrogen, alkyl, aryl, and aralkyl groups; $R_1$ and $R_2$ are individually selected from hydrogen, alkyl, aryl and aralkyl groups; and A is
  (i) —$CH_2$—$CH_2$— or
  (ii) —CH=CH—
comprising the following steps:
  a) reacting 17-carboxylic acid-3-oxo-4-azasteroid of formula 3

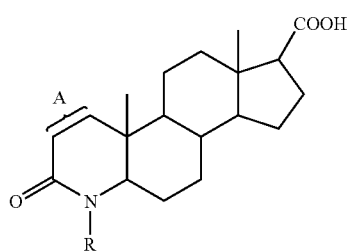

wherein R and A are as defined above, with a compound of formula 4

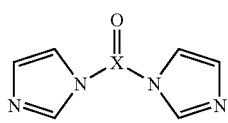

wherein X is C or S; to generate a compound of formula 5

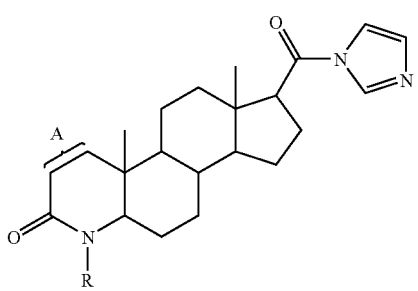

wherein R and A are as defined above; and
  b) reacting the compound of formula 5 with an amine of formula $R_1R_2NH$, wherein $R_1$ and $R_2$ are as defined as above, in the presence of a heterocyclic hydroxyl compound activator.

Surprisingly, we have discovered that 17-carboxylic acid-3-oxo-4-azasteroid of formula 3 can be converted to the corresponding 17-amido compound of formula 2 in high yield and purity by a) converting 3 to its imidazolide 5, and b) reacting imidazolide 5 with an amine in the presence of a heterocyclic hydroxyl compound activator. This process avoids the use of expensive and moisture sensitive organomagnesium halide during the amide formation step and only requires a catalytic amount of heterocyclic hydroxyl compound. Therefore, this process is more desirable for commercial scale production.

More specifically, the imidazolide intermediate 5 can be prepared by reacting carboxylic acid 3 with 1,1'-carbonyldiimidazole (4, X=C) or 1,1'-sulfonyidiimidazole (4, X=S). The carboxylic acid 3 and 1,1'-carbonyldiimidazole or 1,1'-sulfonyidiimidazole are readily available starting materials or can be synthesized by processes known in the art. For example, 1,1'-carbonyidiimidazole can be prepared by reacting phosgene with imidazole, and 1,1'-sulfonyldiimidazole can be synthesized by reacting imidazole with thionyl chloride. The 1,1'-carbonyidiimidazole or 1,1'-sulfonyidiimidazole intermediate thus formed may be isolated or used directly without isolation for the process.

The heterocyclic hydroxyl compound activator can be selected from the 1-hydroxybenzotriazoles and hydroxyridines. Examples of such heterocyclic hydroxyl compounds may include: 1-hydroxybenzotriazole (HOBt), 6-chloro-1-hydroxybenzotriazole (Cl—HOBt), 1-hydroxyl-7-azabenzotriazole (HOAt), 2-hydroxypyridine (HOPy), 2-hydroxy-5-nitropyridine and endo-N-hydroxy-5-norbornene-2,3-dicarboximide (HONB). The preferred compounds are 2-hydroxypyridine and 2-hydroxy-5-nitropyridine.

The imidazolide formation can be carried out in a solvent from about −50° C. to 100° C. and preferably −10° C. to 50° C. Suitable solvents may be selected from chlorinated hydrocarbons, alkyl and aryl nitriles, cyclic or acyclic ethers, alkyl cyclic and acyclic amides, cyclic or acyclic alkyl sulfoxides and sulfones; and aromatics. Examples of such solvents may include: dichloromethane, dichloroethane, chlorobenzene, acetonitrile, 1,2-dimethoxyethane, dimethoxymethane, tetrahydrofuran and 1,4-dioxane, N,N-dimethylformamide, N,N-dimethylacetamide, 1-methyl-2-pyrrolidinone, dimethylsulfoxide, tetramethylene sulfone, toluene and xylenes The preferred solvents are dichloromethane, N,N-dimethylformamide, N,N-dimethylacetamide and 1-methyl-2-pyrrolidinone.

The imidazolide intermediate 5 may be isolated from the reaction mixture and used for the next step, or it can be used directly without isolation. The one-pot approach is more preferable since it employs less solvent, reduces production time, and the overall yield is higher.

The reaction of imidazolide 5 with the amine may be carried out in the same solvent as the imidazolide step, or a different solvent selected from chlorinated hydrocarbons, alkyl and aryl nitriles, cyclic or acyclic ethers, alkyl cyclic and acyclic amides, cyclic or acyclic alkyl sulfoxides and sulfones; and aromatics. Examples of such solvents may include: dichloromethane, dichloroethane, chlorobenzene, acetonitrile, 1,2-dimethoxyethane, dimethoxymethane, tetrahydrofuran and 1,4-dioxane, N,N-dimethylformamide, N,N-dimethylacetamide, 1-methyl-2-pyrrolidinone, dimethylsulfoxide, tetramethylene sulfone, toluene and xylenes. The preferred solvents are dichloromethane, N,N-dimethylformamide, N,N-dimethylacetamide and 1-methyl-2-pyrrolidinone. The reaction temperature may range from about 0° C. to 200° C., and preferably 50° C. to 150° C.

According to another aspect of the present invention, a process is provided for the preparation of a compound of formula 6:

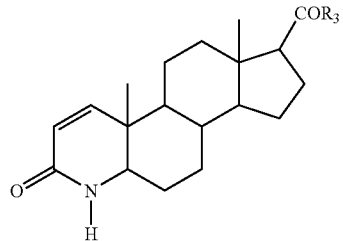

6 wherein $R_3$ is a hydroxyl, OR4, $NR_4R_5$, wherein $R_4$ is a straight or branched C1-C9 alkyl group (for example ethyl, propyl, butyl, iso-butyl, etc.), cycloalkyl containing optionally one or more heteroatoms selected from S, O, N; C10-C20 polycycloalkyl, and aryl; $R_5$ is hydrogen, a straight or branched C1-C9 alkyl group, cycloalkyl containing optionally one or more heteroatoms selected from S, O, N, C10-C20 polycycloalkyl, and aryl; said process comprising the steps of:

a) protecting the amide nitrogen at position 4 of compound of formula 7

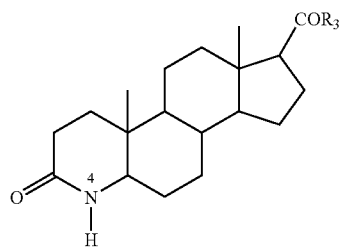

7 with a protecting group P to produce a compound of formula 8;

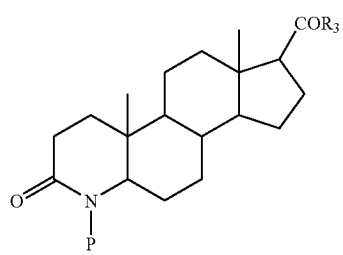

8 wherein $R_3$ is as defined above and P is a protecting group selected from alkyloxycarbonyl, aryloxycarbonyl, aralkyloxycarbonyl, acyl, alkyl, aryl, aralkyl, silyl, sulfenyl and sulfonyl groups, more preferably methoxycarbonyl, ethoxycarbonyl, t-butoxycarbonyl, benzoxycarbonyl, t-amyloxycarbonyl, cyclohexylcarbonyl and isobutoxycarbonyl groups.

b) sulfenylation or sulfinylation in the presence of a solvent and a base or a mixture of bases to produce a compound of formula 9;

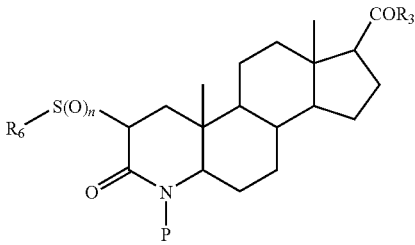

9 wherein $R_3$ and P are as defined above, n is 0 or 1, and $R_6$ is selected from aryl, alkyl and aralkyl groups;

c) oxidation when n is 0 to form compound 9 wherein n is 1 or 2;

d) elimination of the $R_6S(O)_n$— group to introduce a 1,2-double bond; and e) removal of the protecting group P.

The step e) can optionally be performed after step b) or step c).

The present invention provides a new process to introduce a 1,2-double bond to 3-oxo-4-azasteroids through protection, sulfenylation/sulfinylation, optional oxidation, elimination and deprotection. The sulfenylation/sulfinylation is carried out under mild conditions, which prevents potential decomposition and epimerization. The compound is produced in good yield and high purity.

Protection of the amide nitrogen at position 4 of compound of formula 7 may be carried out according to the procedures described in the prior art, for example, the procedures described in, and hereby incorporated as reference, *Protective Groups in Organic Synthesis*, Second Edition, by Greene, T. W. and Wuts, P. G. M., John Wiley & Sons, Inc., 1999, pp. 494-653. The preferred procedure for the formation of the carbamates is the reaction of compound 7 with alkyl or aryl chloroformate or dialkyl or diaryl dicarbonate in the presence of a base or a mixture of bases in a suitable solvent or solvent mixture.

The compound 8 may be isolated from the reaction mixture and used for the next step, or can be used directly without isolation. The one-pot approach is most preferred since it employs less solvent, requires a shorter production time, and the overall yield obtained is higher.

α-Sulfenylation or α-sulfinylation of the carbonyl group of the lactam moiety in compound 8 may be carried out according to the procedures disclosed in the prior art, for example, those disclosed in, and hereby incorporated as reference, *Sulfur Reagents in Organic Synthesis*, by P. Metzner and A. Thuillier, Academic Press, 1994, pp 53-57. The preferred procedure is the reaction of 8 with a sulfenylation or sulfinylation reagent in the presence of a base or a mixture of bases. The suitable sulfenylation reagents may be selected from diaryl disulfides, dialkyl disulfides and thiosulfonates. The preferred sulfenylation reagents are diphenyl disulfide, dimethyl disulfide and S-phenyl benzenethiosulfonate. The preferred sulfinylation reagents are arylsulfinates. Examples of sulfinylation reagents are methyl 2-pyridinesulfinate and methyl phenylsulfinate. The preferred bases are lithium diisopropylamide (LDA), sodium bis(trimethylsilyl)amide (NaHMDS), lithium bis(trimethylsilyl)amide (LiHMDS) and potassium bis(trimethylsilyl)amide (KHMDS).

The sulfenylation product 9 (when n=0) is subject to oxidation to give a compound 9 with n=1 or 2. The sulfinylation product 9 wherein n is 1 can be directly subjected to elimination (step d) and deprotection (step e) to produce the compound 6. The oxidized group is then eliminated typically followed by N-deprotection to produce the compound 6. However, the N-deprotection (step e) can optionally be done after step b) (sulfenylation or sulfinylation) or step c) (oxidation).

The suitable reagents for oxidation may be selected from alkali-metal periodate, alkali-metal perborate, OXONE®, and hydrogen peroxide. The preferred reagents are sodium periodate, sodium perborate and OXONE®. The suitable solvents for the oxidation step are water, C1 to C6 alkyl alcohols, aromatics, cyclic ether solvents and mixtures therefore. The preferred solvents are water, methanol, ethanol, isopropanol, toluene and xylenes. The reaction may be performed at about −20° C. to 150° C., more preferably at 0° C. to 100° C.

The elimination step may be carried out in a solvent or mixture of solvents in the presence or absence of a base. The suitable bases may be selected from organic and inorganic bases, and preferred bases are alkali-metal carbonates and alkali-metal bicarbonates. The suitable solvents may be selected from aromatic and alkyl ketones. The preferred solvents are toluene, xylenes, acetone, methyl ethyl ketone and methyl isobutyl ketone. The reaction is performed at about −20° C. to 200° C., most preferably at 0° C. to 100° C.

The N-deprotection step may be carried out according to the procedures disclosed in the prior art (Greene, T. W. and Wuts, P. G. M., 'Chapter 7. Protection for the Amino Group', in "Protective Groups in Organic Synthesis", Second Edition, John Wiley & Sons, Inc., 1999, pp. 494-653). For example, when t-butoxycarbonyl is used as protecting group, the preferred deprotecting procedure is treatment with an acid.

Further, according to another aspect of the present invention, a process is provided for the preparation of compound formula 1:

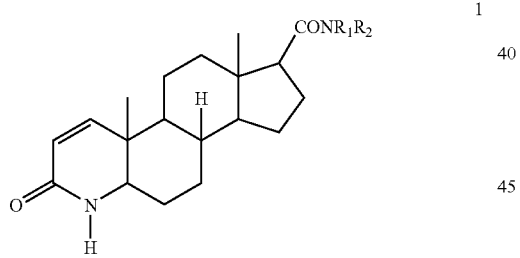

1 comprising the steps of:
a) reacting 17-carboxylic acid-3-oxo-4-azasteroid of formula 10

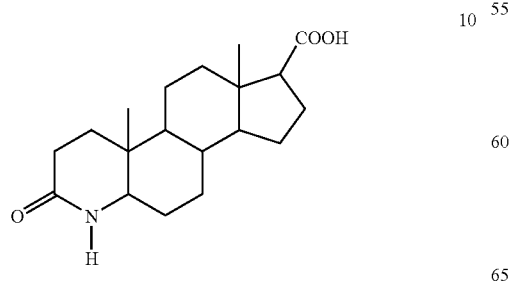

10 with a compound of formula 4

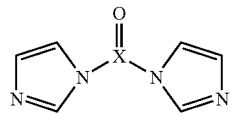

4 wherein X is C or S, to form a product of formula 11

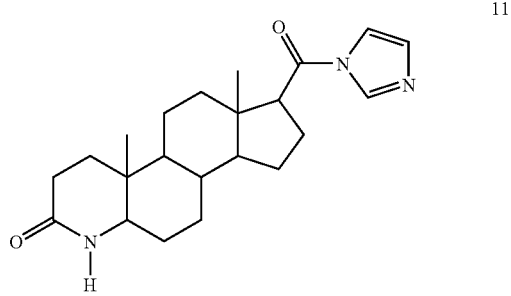

11 b) reacting the compound of formula 11 with an amine of formula $R_1R_2NH$, wherein $R_1$ and $R_2$ are individually selected from hydrogen, alkyl, aryl and aralkyl groups, in the presence of a heterocyclic hydroxyl activator compound to produce a compound of formula 12:

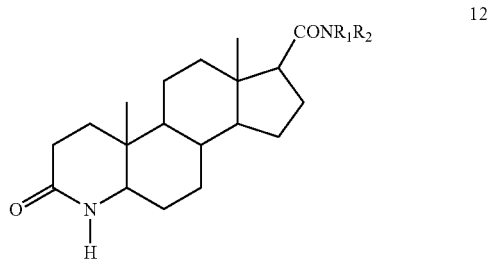

12 c) protecting the NH of the compound of formula 12 to produce a compound of formula 13:

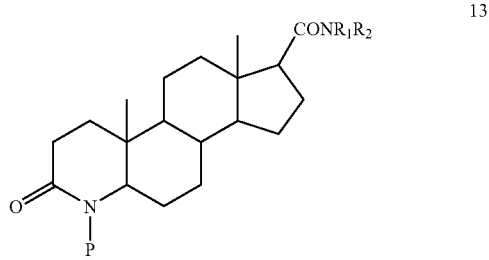

13 wherein $R_1$ and $R_2$ are as defined above, and P is a protecting group selected from alkyloxycarbonyl, aryloxycarbonyl, aralkyloxycarbonyl, acyl, alkyl, aryl, aralkyl, silyl, sulfenyl and sulfonyl, more preferably from methoxycarbonyl, ethoxycarbonyl, t-butoxycarbonyl, benzoxycarbonyl, t-amyloxycarbonyl, cyclohexylcarbonyl and isobutoxycarbonyl groups;

d) sulfenylation or sulfinylation in the presence of a solvent and a base or mixture of bases, to produce the compound of formula 14:

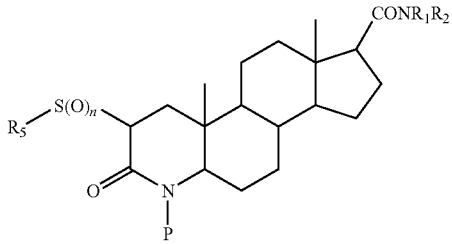

wherein $R_1$, $R_2$ and P are as defined above, n is 0 or 1, and $R_5$ is selected from aryl, alkyl and aralkyl groups;

e) oxidation when n is 0 to form compound 14 in which n is 1 or 2;

f) elimination of the $R_5S(O)_n$— group to introduce a 1,2-double bond; and g) removing the protecting group P.

The step g) can be performed after step d) or step e).

The detailed reaction conditions are the same as disclosed in the previous sections of this invention.

Overall using the processes of the instant invention, a new method for the preparation of 17-N-substituted-carbamoyl-4-aza-androst-1-en-3-ones is achieved. The processes overcome the deficiencies of the prior art by using less- or non-toxic reagents and mild reaction conditions. Equally important, these processes are safe and robust, and yield pure material, suitable for use as pharmaceuticals. These processes are particularly useful for the production of Finasteride and Dutasteride.

The following non-limiting examples further illustrate the manner of carrying out the invention described herein.

EXAMPLES

Example 1

N-tert-Butyl-3-oxo4-aza-5α-androstane-17β-carboxamide

To a stirring mixture of 3-oxo-4-aza-5α-androstane-17β-carboxylic acid (20 g, 62.6 mmol) in dry N-methyl-2-pyrrolidinone (100 mL) was added 1,1'-carbonyldiimidazole (11.2 g, 68.9 mmol) and the reaction mixture was stirred at controlled room temperature (20-30° C.). After 5 hours, HPLC analysis showed no remaining starting material and the reaction mixture was placed into a high pressure vessel along with 2-hydroxypyridine (3.0 g, 31.3 mmol) and tert-butylamine (9.2 g, 125.2 mmol). With an oil bath temperature of 100° C. and an internal pressure of 10-20 psi, the reaction mixture was stirred. After 6 hours, TLC analysis showed no remaining starting material, and the reaction mixture was cooled to room temperature (20-25° C.), charged with deionized water (100 mL) and stirred at 5-10° C. for 4 hours. The resulting slurry was filtered and washed with deionized water. To this solid was added deionized water (200 mL) and the resulting slurry was stirred at room temperature for 3 hours, filtered, washed with deionized water and dried under high vacuum at 50-60° C. for 16 hours to afford 21.1 g (90% yield) of N-tert-butyl-3-oxo-4-aza-5α-androstane-17β-carboxamide as an off-white solid.

Example 2

N-tert-Butyl-2-phenylsulfenyl-3-oxo4-aza-5α-androstane-17β-carboxamide

N-tert-Butyl-3-oxo-4-aza-5α-androstane-17β-carboxamide (10 g, 26.7 mmol) obtained from example 1 was added to dry tetrahydrofuran (100 mL) and the resulting slurry was cooled to −20° C. Lithium bis(trimethylsilyl)amide in tetrahydrofuran (24 wt % in THF) (22.3 g, 32.0 mmol) was added dropwise to the mixture, and the resulting slurry was stirred at −20° C. for 30 minutes. To the slurry was added di-tert-butyl-dicarbonate (6.4 g, 29.3 mmol) in portions at −20° C. After 1 hour, TLC and HPLC analyses indicated the absence of starting material, and the reaction mixture was charged with phenyl disulfide (6.4 g, 29.4 mmol). Lithium bis(trimethylsilyl)amide in tetrahydrofuran (24 wt % in THF) (27.9 g, 40.0 mmol) was added dropwise, and the resulting reaction mixture was stirred at −20° C. for 2 hours. TLC and HPLC analyses showed no remaining starting material, and the reaction mixture was charged with deionized water (50 mL) and allowed to return to room temperature. The reaction mixture was filtered through Celite®, and washed with ethyl acetate. The organic layer was washed with saturated aqueous sodium bicarbonate and deionized water. The ethyl acetate layer was exchanged with methanol and to the reaction mixture was added IPA/HCl (20 wt % HCl in IPA) (14.6 g, 80.0 mmol), and stirred at room temperature for 16 hours and monitored by TLC. The reaction mixture was neutralized with saturated aqueous sodium bicarbonate, filtered through Celite® and washed with ethyl acetate. The ethyl acetate layer was exchanged with heptanes and to the reaction mixture was added 1:1 v/v methanol/deionized water and stirred at room temperature. The methanol/deionized water layer was distilled to remove methanol, charged with acetone, stirred at room temperature, and the slurry was filtered, washed with deionized water/acetone 5:1 v/v and dried under high vacuum at 50-60° C. for 16 hours to afford 9.0 g (70% yield) of N-tert-butyl-2-phenylsulfenyl-3-oxo-4-aza-5α-androstane-17β-carboxamide as a pale yellow solid.

Example 3

N-tert-Butyl-3-oxo-4-aza-5α-androst-1-en-17β-carboxamide (Finasteride)

Sodium metaperiodate (8.0 g, 37.4 mmol) was added to a solution of N-tert-butyl-2-phenylsulfenyl-3-oxo-4-aza-5α-androstane-17β-carboxamide (9.0 g, 18.6 mmol) obtained from example 2 in methanol (90 mL) and the resulting slurry was stirred at room temperature. Following the dropwise addition of deionized water (18 mL), the reaction mixture was stirred at room temperature. After stirring a further 6 hours, the reaction mixture was filtered, and the precipitate was washed several times with ethyl acetate. Deionized water was then added to the reaction mixture and the layers were separated. The organic layer was evaporated and the residue was dissolved in toluene and the resulting solution was heated to reflux. After 1 hour, the reaction mixture was cooled to room temperature. After the addition of the equivalent volume of heptanes, the reaction slurry was cooled to 0-5° C., maintained for 4-5 hours, filtered, washed with toluene/heptanes 1/1 (v/v) and dried under high vacuum at 50-60° C. for 16 hours to afford 6.0 g (86% yield) of Finasteride.

What is claimed is:

1. A process for the preparation of 17-amido-3-oxo-4-aza-steroid of formula 2

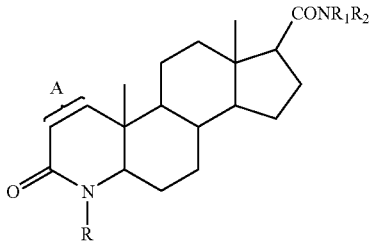

comprising the steps of:
a) reacting in the presence of a solvent 17-carboxylic acid-3-oxo-4-azasteroid of formula 3

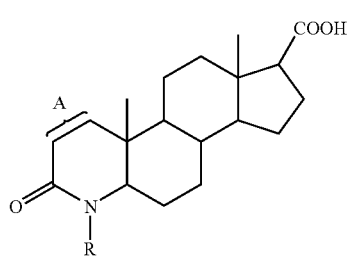

wherein R is selected from hydrogen, alkyl, aryl and aralkyl groups, and A is
(i) —$CH_2CH_2$—, or
(ii) —CH=CH—
with the compound of formula 4

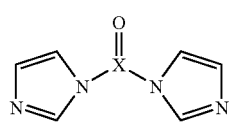

wherein X is C or S, to generate the compound of formula 5

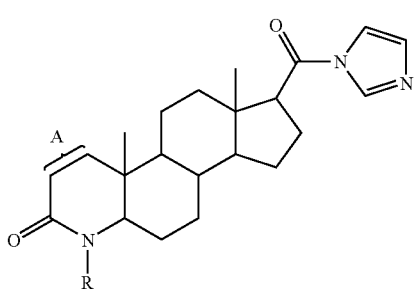

wherein R and A are as defined above; and
b) reacting the compound of formula 5 with an amine of formula $R_1R_2NH$, wherein $R_1$ and $R_2$ are individually selected from hydrogen, alkyl, aryl and aralkyl groups, in the presence of a heterocyclic hydroxyl activator compound.

2. A process according to claim 1 wherein the heterocyclic hydroxyl activator compound is selected from 1-hydroxybenzotriazole (HOBt), 6-chloro-1-hydroxybenzotriazole (Cl—HOBt), 1-hydroxyl-7-azabenzotriazole (HOAt), 2-hydroxypyridine (HOPy), 2-hydroxy-5-nitropyridine and endo-N-hydroxy-5-norbornene-2,3-dicarboximide (HONB).

3. A process according to claim 1 wherein the heterocyclic hydroxyl activator compound is 2-hydroxypyridine or 2-hydroxy-5-nitropyridine.

4. A process according to claim 1 wherein the solvent is selected from chlorinated hydrocarbons; alkyl and aryl nitriles; cyclic or acyclic ethers; alkyl cyclic and acyclic amides; cyclic or acyclic alkyl sulfoxides and sulfones; aromatics; and mixtures thereof.

5. A process according to claim 1 wherein the solvent is dichloromethane, N,N-dimethylformamide, N,N-dimethylacetamide or 1-methyl-2-pyrrolidinone, and mixtures thereof.

6. A process according to claim 1 for the production of Finasteride.

7. A process for the preparation of the compound of formula 6:

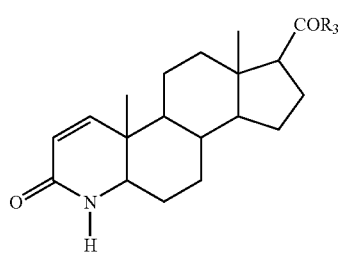

comprising the steps of:
a) protecting the amide nitrogen at position 4 of the compound of formula 7

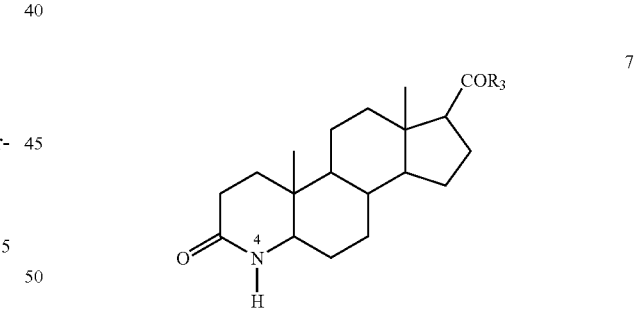

to produce the compound of formula 8

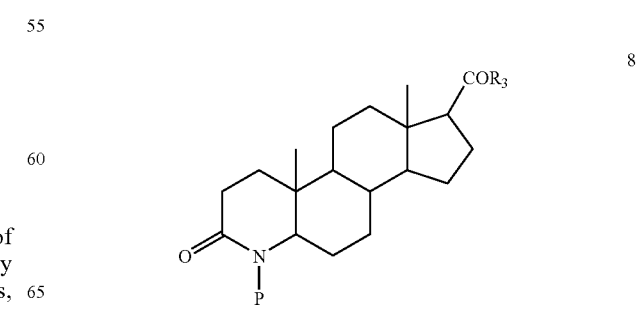

wherein P is a protecting group selected from alkyloxycarbonyl, aryloxycarbonyl, aralkyloxycarbonyl, acyl, alkyl, aryl, aralkyl, silyl, sulfenyl and sulfonyl; $R_3$ is a hydroxyl, $OR_4$, $NR_4R_5$, wherein $R_4$ is a straight or branched C1-C9 alkyl group, cycloalkyl containing optionally one or more heteroatoms selected from S, O, N; C10-C20 polycycloalkyl, and aryl; and $R_5$ is hydrogen, a straight or branched C1-C9 alkyl group, cycloalkyl containing optionally one or more heteroatoms selected from S, O, N, C10-C20 polycycloalkyl, and aryl;

b) sulfenylation or sulfinylation in the presence of a solvent and a base or a mixture of bases to produce the compound of formula 9

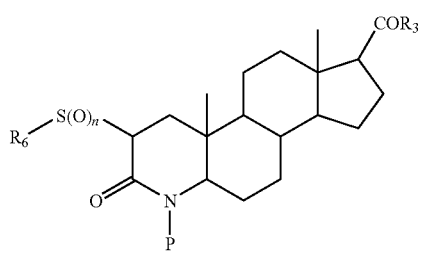

9 wherein $R_3$ and P are as defined above, n is 0 or 1, and $R_6$ is selected from aryl, alkyl and aralkyl groups c) oxidation when n is 0 to form compound 9 wherein n is 1 or 2;

d) elimination of the $R_6S(O)_n$— group to introduce the 1,2-double bond;

e) removing the protecting group P; and f) the step e) can optionally be performed after step b) or step c).

8. A process according to claim 7 wherein the protecting group P is selected from methoxycarbonyl, ethoxycarbonyl, t-butoxycarbonyl, benzoxycarbonyl, t-amyloxycarbonyl, cyclohexylcarbonyl and isobutoxycarbonyl.

9. A process according to claim 7 wherein step b) consists of sulfenylation and the sulfenylation is performed by reacting the compound of formula 8 with a sulfenylation reagent in the presence of a base or a mixture of bases.

10. A process according to claim 7 wherein step b) consists of sulfinylation and the sulfinylation is performed by reacting the compound of formula 8 with a sulfinylation reagent in the presence of a base or a mixture of bases.

11. A process according to claim 7 wherein step b) consists of sulfenylation and the suitable sulfenylation reagents include diaryl disulfides, dialkyl disulfides and thiosulfonates.

12. A process according to claim 7 wherein step b) consists of sulfenylation and the sulfenylation reagent is diphenyl disulfide, dimethyl disulfide or S-phenyl benzenethiosulfonate.

13. A process according to claim 7 wherein step b) consists of sulfinylation and the sulfinylation reagent is methyl 2-pyridinesulfinate or methyl phenylsulfinate.

14. A process according to claim 7 wherein the base used in the sulfenylation or sulfinylation step is selected from lithium diisopropylamide (LDA), sodium bis(trimethylsilyl)amide (NaHMDS), lithium bis(trimethylsilyl)amide (LiHMDS) and potassium bis(trimethylsilyl)amide (KHMDS), or a mixture thereof.

15. A process according to claim 7 wherein the oxidizing reagent used is selected from alkali-metal periodate, alkali-metal perborate, OXONE® and hydrogen peroxide.

16. A process according to claim 7 wherein the elimination step is carried out in a solvent or mixture of solvents in the presence or absence of a base.

17. A process according to claim 7 wherein the suitable bases used in the elimination step are selected from organic and inorganic bases.

18. A process according to claim 7 wherein the bases used in the elimination step are alkali-metal carbonates or alkali-metal bicarbonates.

19. A process according to claim 7 wherein the solvents used in the elimination step are selected from toluene, xylenes, acetone, methyl ethyl ketone and methyl isobutyl ketone, and mixtures thereof.

20. A process according to claim 7 for the production of Finastende.

21. A process for the preparation of the compound of formula 1

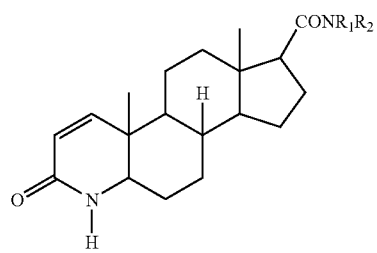

1 comprising the steps of:

a) reacting in the presence of a solvent the 17-carboxylic acid-3-oxo-4-azasteroid of formula 10

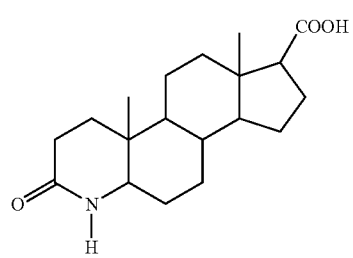

10 with the compound of formula 4

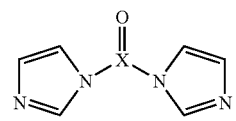

4 wherein X is C or S; to form the product of formula 11

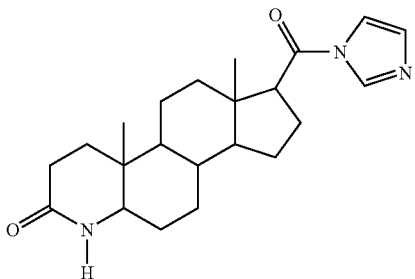

b) reacting the compound of formula 11 with an amine of formula $R_1R_2NH$, wherein $R_1$ and $R_2$ are individually selected from hydrogen, alkyl, aryl and aralkyl groups, in the presence of a heterocyclic hydroxyl activator compound to produce the compound of formula 12

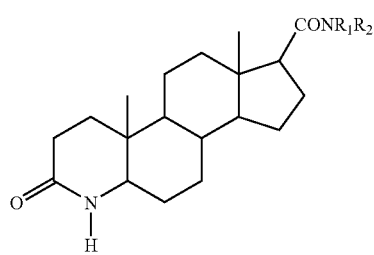

c) protecting the NH of the compound of formula 12 to produce the compound of formula 13

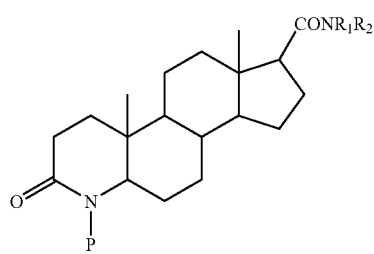

wherein $R_1$ and $R_2$ are as defined above, and P is a protecting group selected from alkyloxycarbonyl, aryloxycarbonyl, aralkyloxycarbonyl, acyl, alkyl, aryl, aralkyl, silyl, sulfenyl and sulfonyl;

d) sulfenylation or sulfinylation in the presence of a solvent and a base or a mixture of bases to produce the compound of formula 14

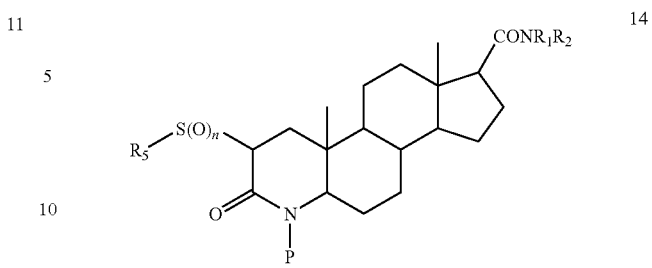

wherein $R_1$, $R_2$ and P are as defined above, n is 0 or 1, and $R_5$ is selected from aryl and alkyl groups;

e) oxidation when n is 0 to form the compound 14 wherein n is 1 or 2;

f) elimination of the $R_5S(O)_2$— group to introduce the 1,2-double bond;

g) removing the protecting group P; and h) the step g) can be performed after step d) or step e).

22. A process according to claim 21 wherein the heterocyclic hydroxyl activator compound is selected from 1-hydroxybenzotriazole (HOBt), 6-chloro-1-hydroxybenzotriazole (Cl—HOBt), 1-hydroxyl-7-azabenzotriazole (HOAt), 2-hydroxypyridine (HOPy), 2-hydroxy-5-nitropyridine and endo-N-hydroxy-5-norbornene-2,3-dicarboximide (HONB).

23. A process according to claim 21 wherein the heterocyclic hydroxyl activator compound is 2-hydroxypyridine or 2-hydroxy-5-nitropyridine.

24. A process according to claim 21 wherein the solvent used in steps a) and b) is selected from chlorinated hydrocarbons; alkyl and aryl nitriles; cyclic or acyclic ethers; alkyl cyclic and acyclic amides; cyclic or acyclic alkyl sulfoxides and sulfones; aromatics; and mixtures thereof.

25. A process according to claim 21 wherein the solvent used in steps a) and b) is selected from dichloromethane, N,N-dimethylformamide, N,N-dimethylacetamide and 1-methyl-2-pyrrolidinone, and mixtures thereof.

26. A process according to claim 21 wherein the protecting group P is selected from methoxycarbonyl, ethoxycarbonyl, t-butoxycarbonyl, benzoxycarbonyl, t-amyloxycarbonyl, cyclohexyloxycarbonyl and isobutoxycarbonyl.

27. A process according to claim 21 wherein step d) consists of sulfenylation and the sulfenylation procedure is the reaction of 13 with a sulfenylation reagent in the presence of a base or a mixture of bases.

28. A process according to claim 21 wherein step d) consists of sulfinylation and the sulfinylation procedure is the reaction of 13 with a sulfinylation reagent in the presence of a base or a mixture of bases.

29. A process according to claim 21 wherein step d) consists of sutfenylatlon and the suitable sulfenylation reagents are selected from diaryl disulfides, dialkyl disulfides and thiosulfonates.

30. A process according to claim 21 wherein step d) consists of sulfenylation and the sulfenylation reagents are selected from diphenyl disulfide, dimethyl disulfide and S-phenyl benzenethiosulfonate.

31. A process according to claim 21 wherein step d) consists of sulfinylation and the sulfinylation reagents are selected from methyl 2-pyridinesulfinate and methyl phenylsulfinate.

32. A process according to claim 21 wherein the base used in the sulfenylation or sulfinylation step is selected from lithium diisopropylamide (LDA), sodium bis(trimethylsilyl)

amide (NaHMDS), lithium bis(trimethylsilyl)amide (LiHMDS) and potassium bis(trimethylsilyl)amide (KHMDS), and a mixture thereof.

33. A process according to claim 21 wherein the oxidizing reagent used is selected from alkali-metal periodate, alkali-metal perborate, OXONE® and hydrogen peroxide.

34. A process according to claim 21 wherein the suitable bases used in the elimination step include organic and inorganic bases.

35. A process according to claim 21 wherein the bases used in the elimination step are alkali-metal carbonates and alkali-metal bicarbonates.

36. A process according to claim 21 wherein the solvents used in the elimination step are selected from toluene, xylenes, acetone, methyl ethyl ketone and methyl isobutyl ketone, and mixtures thereof.

37. A process according to claims 21 for the production of Finasteride.

38. The process according to claim 1 wherein the solvent is selected from dichloromethane, dichioroethane, chloroberizene, acetonitrile, 1,2-dimethoxyethane, dimethoxymethane, tetrahydrofuran, 1,4-dioxane; N,N-dimethylformamide, N,N-dimethylacetamide, 1-methyl-2-pyrrolidinone; dimethylsulfoxide and tetramethylene sulfone, toluene, xylenes and mixtures thereof.

39. The process according to claim 21 wherein the solvent used in steps a) and b) is selected from dichioromethane, dichloroethane, chlorobenzene; acetonitrile, 1,2-dimethoxyethane, dimethoxymethane, tetrahydrofuran, 1,4-dioxane, N,N-dimethylformamide, N,N-dimethylacetamide, 1-methyl-2-pyrrolidinone, dimethylsulfoxide and tetramethylene sulfone, toluene, xylenes, and mixtures thereof.

* * * * *